United States Patent [19]

Kopf

[11] 4,250,742
[45] Feb. 17, 1981

[54] METHOD AND APPARATUS FOR TESTING HARDNESS OF HOMOGENEOUS MATERIALS

[75] Inventor: Rowland J. Kopf, Southington, Conn.
[73] Assignee: Densicon Associates, Hamden, Conn.
[21] Appl. No.: 93,133
[22] Filed: Nov. 9, 1979
[51] Int. Cl.³ .............................................. G01N 3/48
[52] U.S. Cl. .......................................... 73/82; 73/85; 227/10
[58] Field of Search ................... 73/82, 81, 85; 227/9, 227/10, 11

[56] References Cited

U.S. PATENT DOCUMENTS

| | | | |
|---|---|---|---|
| 3,297,224 | 1/1967 | Osborne | 227/10 |
| 3,894,426 | 7/1975 | Kopf | 73/82 |
| 3,972,229 | 8/1976 | Kopf | 73/85 |

FOREIGN PATENT DOCUMENTS 272232  7/1970  U.S.S.R. ..................................... 73/82

Primary Examiner—Donald O. Woodiel
Attorney, Agent, or Firm—William W. Jones

[57] ABSTRACT

A powder-actuated apparatus for determining the hardness of various homogeneous materials wherein the determination may be made in a manufacturing facility, warehouse, or in the field. The apparatus ensures that a constant driving force will be delivered to a testing probe without the need to carefully control the energy input source for the apparatus. Thus, conventional cased or caseless powder charges can be used as the initial energy source for the apparatus.

7 Claims, 1 Drawing Figure

U.S. Patent     Feb. 17, 1981     4,250,742
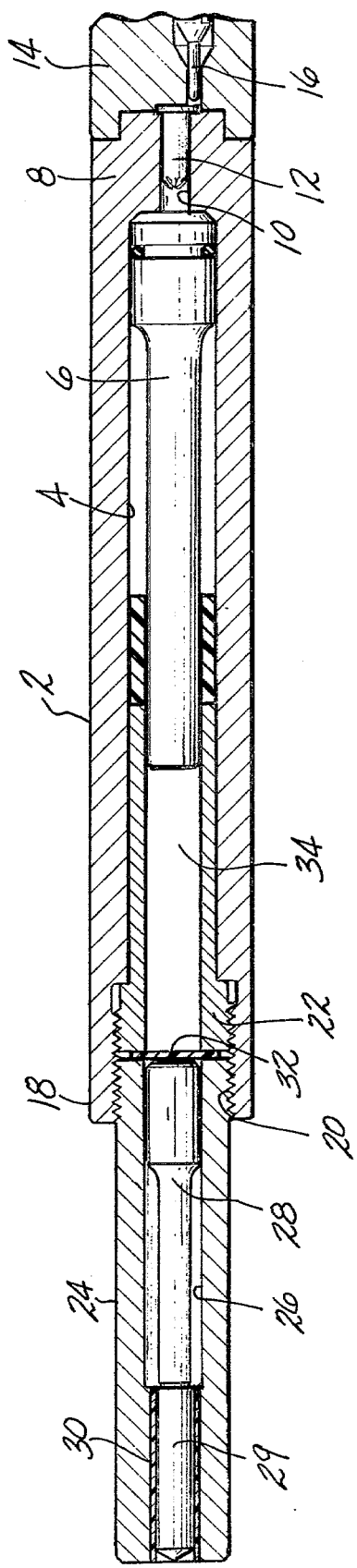

METHOD AND APPARATUS FOR TESTING HARDNESS OF HOMOGENEOUS MATERIALS

This invention relates to an improved apparatus for use in testing the hardness of various homogeneous materials, such as building blocks, mortar, brick, ceramic, cement and concrete patch materials, metals, refractories, and the like. More particularly, the apparatus of this invention is an improved powder-actuated tool which drives a probe into the material being tested, whereby probe penetration is measured in order to determine material hardness. Means are provided in the tool to deliver a constant, controlled driving force to the probe while, at the same time, allowing the use of conventional powder charges as the energy source for the tool.

A system has been designed which permits the determination of the hardness of many homogeneous materials in the manufacturing plant, in the warehouse, or in the field. The system utilizes a powder-actuated tool, of the piston type, which is used to drive a probe into the material being tested. The depth of probe penetration into the material is measured thereby providing means for determining the hardness of the material. Details of this system are disclosed in U.S. Pat. No. 3,894,426, issued July 15, 1975 to Rowland J. Kopf; and U.S. Pat. No. 3,972,229, issued Aug. 3, 1976 to Rowland J. Kopf.

One problem which has arisen in connection with the system described above relates to the force with which the probe is driven into the material being tested. It is apparent that the validity of the test results observed depend on the provision of a constant driving force for the probe. If the driving force varies from test to test, then obviously, the depth of penetration of the probe will vary proportionally therewith, making the results of the test invalid unless the initial driving force for each shot is known and proportional adjustments are made.

Since the apparatus used in performing the test is a powder-actuated tool, the prior art noted above deals with the problem of variation of energy output from one powder charge to the next by specifying that the charges used must be carefully controlled in size, weight, and grain, so as to always provide the same energy output when fired. This approach, in connection with cased charges, requires that the equivalent of "match" ammunition, in blank form, of course, be used. This greatly increases the cost of the ammunition used, since very careful metering of exactly blended powder charges and primer charges must be ensured.

In order to avoid this problem and the cost associated with its solution in connection with cased charges, the prior art cited above suggests that caseless propellant charges be used. Theoretically, the caseless charges can be more accurately formed from a blend and dimensional standpoint, and thus will provide a constant power output. In fact, however, it has been found that caseless charges will absorb ambient moisture, flake and chip, and will not, without extremely careful packaging and handling, provide constant power output when fired. Furthermore, caseless cartridges require specialized tools with specialized firing chambers for use.

I have solved the problem of inconsistent propellant charge energy without requiring special powder charges being used. With the improved tool of my invention, ordinary and conventional cased charges used with any conventional piston type powder-actuated tool may be utilized. Moreover, my system for providing constant driving force for the probe can be used in conjunction with a conventional powder-actuated piston tool of the general type disclosed in U.S. Pat. No. 3,297,224, issued Jan. 10, 1967 to W. E. Osborne. This type of piston tool is modified by being provided with a gas pressure chamber at its muzzle end. A secondary sub-assembly containing a driving piston and the probe-sleeve combination is connected to the muzzle end of the tool. Between the gas pressure chamber and the driving piston, there is positioned a driving pressure regulator, preferably a burst disk which will burst under a given pressure. Once the bursting pressure is reached in the pressure chamber, the disk bursts and the bursting pressure is immediately applied to the driving piston. The characteristics of the burst disk can be accurately controlled so that it will burst when substantially the same pressure is applied to it, thus substantially the same driving pressure is consistantly delivered to the driving piston for embedding the probe in the material being tested, from shot to shot. If a higher or lower pressure is desired for driving the probe into any particular material being tested, the proper driving pressure can be provided by varying the burst pressure of the disk. Thus, greater driving force can be delivered to the probe by making the disk thicker.

It is, therefore, an object of this invention to provide an apparatus for driving a probe into a mass of homogeneous material to determine the hardness of the material being tested.

It is a further object of this invention to provide an apparatus of the character described wherein a controllable and constant driving force is delivered to a probe.

It is yet another object of this invention to provide an apparatus of the character described which incorporates a powder-actuated piston-type tool for producing operating energy for driving the probe.

It is an additional object to provide an apparatus of the character described which is completely portable and wherein the driving force delivered to the probe can be increased or decreased depending on the material being tested.

These and other objects and advantages of this invention will be readily appreciated from the following detailed description of a preferred embodiment thereof taken in conjunction with the accompanying drawing.

The drawing is an axial sectional view of a portion of a powder-actuated tool formed in accordance with this invention. Referring now to the drawing, the tool comprises a main barrel 2 having a bore 4 in which a piston 6 is mounted for reciprocal axial movement. This piston 6 is shown in the drawing in its firing position. The barrel 2 includes a breech end 8 containing a firing chamber 10 in which there is positioned a conventional cased powder charge 12 of the type used with powder-actuated tools. The tool includes a breech closure member 14 containing a firing pin 16 which will be operated by means of a trigger assembly (not shown), a hammer, or any other operative means used to fire cartridges.

The barrel 2 also includes a muzzle end 18 having an internal threaded bore 20. A sleeve 22 may be threaded into the bore 20, the sleeve 22 extending toward the breech end 8 of the barrel 2 so that the muzzle end of the piston 6, as is shown in the drawing, extends into the sleeve 22. The sleeve 22 is particularly useful in adapting a conventional piston tool of the type having a pawl slot for returning the piston from a fired position to a firing position for use in connection with this invention.

If no return slot is present in the tool barrel, the sleeve 22 may be omitted.

Also threaded into the bore 20 is a barrel member 24 having a bore 26 in which there is slidably mounted a piston 28 which is shown in the drawing in its driving position. Seated in the muzzle end of the barrel member 24 is the testing subassembly which consists of the probe 29 fitted with a sleeve 30. The probe-sleeve assembly is made in accordance with the teachings of U.S. Pat. No. 3,972,229, referred to previously. A burst disk 32 is sandwiched between the sleeve 22 and the barrel 24, and firmly held in place therein. The disk 32 is preferably made of plastic material and is constructed so as to predictably burst when subjected to a predetermined gas pressure. The burst pressure required can be changed by changing the thickness of the disk 32. Metal, polyethylene, Nylon, Teflon (trademark), compressed fibers, or Mylar (trademark) have been found to be suitable for making the disk 32.

For purposes of description, the piston 28 is referred to as the driving piston, and the piston 6 is referred to as the compression piston. Forward of the compression piston 6 within the sleeve 22, there is defined a compression chamber 34. The compression chamber 34 is bounded by the compression piston 6, the sleeve 22, and the burst disk 32. It will be understood that the driving piston 28 is positioned in its driving position by inserting a new probe-sleeve combination into the muzzle end of the barrel 24. As shown in the drawing, the device is ready to operate.

The device is operated by positioning the muzzle end of the barrel 24 squarely against the surface of the material being tested. The cartridge 12 is fired whereby the compression piston 6 is driven toward the muzzle end of the tool. Forward movement of the driving piston 6 causes compression of the air within the compression chamber 34, which compression continues until the pressure needed to burst the disk 32 is achieved. Once burst pressure is achieved, the disk 32 ruptures and the pressurized air is delivered to the driving piston 28 to drive the latter against the probe 29. It will be appreciated that the blast of pressurized air is always controlled as to pressure which is dependent upon the pressure needed to burst or rupture the disk 32. Thus, a constant driving force is delivered to the driving piston 28. Any variations in energy output of the cartridges used in the tool will not affect the driving force delivered to the driving piston 28, but may merely cause slight variations in the time lag between firing of the cartridges and the attainment of bursting pressure in the pressure chamber 34.

From the preceding, it will be readily appreciated that the device of this invention will provide a constant driving force to a testing probe so that imbedment of the probe in the material being tested will accurately reflect the hardness of the material being tested. The driving force can be controlled by simply altering the characteristics of the burst disk. Furthermore, the device is completely portable and does not require precisely controlled powder charges for proper operation Since many changes and variations of the disclosed embodiment of the invention may be made without departing from the inventive concept, it is not intended to limit the invention otherwise than as required by the appended claims.

What is claimed is:

1. A powder-actuated tool for providing a substantially constant driving force for driving a probe into a mass of homogeneous material to determine the hardness of the material, said tool comprising:
    (a) a first piston slidably mounted in a barrel;
    (b) means forming a compression chamber, said compression chamber containing a compressible fluid which is compressed to a predetermined driving pressure when said first piston is moved from a driving position within said barrel;
    (c) means associated with said barrel for firing a powder charge to move said first piston from said driving position within said barrel;
    (d) holder means operably associated with said barrel, said holder means having a bore for receiving the probe to be driven into the material being tested;
    (e) a driving piston movably mounted in said holder means for driving the probe into the material being tested; and
    (f) means for delivering a substantially constant driving force from said compression chamber to said driving piston only upon attainment of said driving pressure in said compression chamber.

2. A powder-actuated tool for driving a probe into a mass of homogeneous material to determine the hardness of the material, said tool comprising:
    (a) a first barrel having a bore;
    (b) means forming a cartridge chamber communicating with one end of said first barrel bore;
    (c) means associated with said cartridge chamber for firing a powder charge disposed in said cartridge chamber;
    (d) a compression piston slidably mounted in said first barrel bore;
    (e) means forming a compression chamber associated with said first barrel, said compression chamber containing a compressible fluid which is compressed to a predetermined driving pressure when said compression piston is moved from a driving position within said first barrel bore;
    (f) a member associated with said first barrel, said member having a bore for receiving the probe to be driven into the material being tested;
    (g) a driving piston slidably mounted in said member bore for driving the probe into the material being tested; and
    (h) a rupturable disk mounted between said compression chamber and said member bore, said disk being operable to burst upon attainment of said driving pressure in said compression chamber whereby a constant driving force will be delivered to said driving piston when the tool is actuated.

3. A powder-actuated tool for driving a probe into a mass of homogeneous material to determine the hardness of the material, said tool comprising:
    (a) a first barrel having a bore, said first barrel having a breech end and a muzzle end opposite said breech end, and said first barrel having a cartridge chamber formed in said breech end, said cartridge chamber communicating with said bore;
    (b) a breech block for closing said breech end of said first barrel, said breech block containing means for firing a cartridge disposed in said cartridge chamber;
    (c) a first piston slidably disposed in said first barrel bore, said first piston being movable within said first barrel bore from a driving position adjacent said breech end of said first barrel through a driving stroke toward said muzzle end of said first barrel;

(d) means forming a compression chamber in said first barrel, said compression chamber opening into said first barrel bore whereby air in said compression chamber will be compressed to a predetermined driving pressure upon movement of said first piston through its driving stroke;

(e) a rupturable disk sealing an outlet end of said compression chamber;

(f) a second barrel secured to said first barrel, said second barrel having a bore for receiving a probe therein;

(g) a drive piston slidably mounted in said second barrel bore for driving said probe into the material being tested; and (h) means forming a gas passage between said disk and said drive piston whereby said drive piston will be actuated to drive said probe by compressed air upon rupture of said disk.

4. A method of driving a probe into a mass of homogeneous material for testing the hardness of the material, said method comprising:

(a) providing a compression chamber;

(b) providing a rupturable disk closing one end of said compression chamber;

(c) providing a driving piston outside of said compression chamber and adjacent to said rupturable disk;

(d) increasing air pressure within said compression chamber to a predetermined pressure whereby said rupturable disk ruptures; and (e) directing air flowing through said ruptured disk against said driving piston to drive the latter against a probe whereby the probe is driven into the material being tested.

5. The method of claim 4, wherein air pressure within said compression chamber is increased by driving a piston into said compression chamber to decrease the volume thereof.

6. An apparatus for driving a probe into a mass of homogeneous material for testing the hardness of the material, said apparatus comprising:

(a) means forming an air compression chamber;

(b) a rupturable disk closing an outlet end of said compression chamber;

(c) a drive piston mounted in a housing adjacent to said rupturable disk and outside of said compression chamber;

(d) means associated with said housing for receiving the probe in alignment with said drive piston;

(e) means for increasing the air pressure in said compression chamber to a predermined pressure to rupture said rupturable disk; and (f) means for venting compressed air flowing through the ruptured disk to said drive piston to drive the latter against the probe.

7. The apparatus of claim 6, wherein said means for increasing the air pressure in said compression chamber comprises a compression piston and powder-actuated means for driving said compression piston into said compression chamber to reduce the volume thereof.

* * * * *